US007372566B2

(12) United States Patent
Vesey et al.

(10) Patent No.: US 7,372,566 B2
(45) Date of Patent: May 13, 2008

(54) CYTOMETER (75) Inventors: Graham Vesey, Hornsby (AU); Mark Gauci, Fairlight (AU); Paul Begini, Penrith (AU); Nicholas Hermann, Leura (AU)

(73) Assignee: BTF PTY Ltd., New South Wales (AU)

( * ) Notice: Subject to any disclaimer, the term of this patent is extended or adjusted under 35 U.S.C. 154(b) by 393 days.

(21) Appl. No.: 10/493,573

(22) PCT Filed: Oct. 25, 2002

(86) PCT No.: PCT/AU02/01454

§ 371 (c)(1),
(2), (4) Date: Nov. 1, 2004

(87) PCT Pub. No.: WO03/036273

PCT Pub. Date: May 1, 2003

(65) Prior Publication Data
US 2005/0062956 A1 Mar. 24, 2005

(30) Foreign Application Priority Data
Oct. 26, 2001 (AU) .................................... PR8465

(51) Int. Cl.
*G01N 21/00* (2006.01)
(52) U.S. Cl. ...................................... 356/338; 356/342
(58) Field of Classification Search ................ 356/338, 356/339, 342
See application file for complete search history.

(56) References Cited
U.S. PATENT DOCUMENTS
3,560,754 A * 2/1971 Kamentsky .................. 209/559

| 3,710,933 | A | * | 1/1973 | Fulwyler et al. | ............. 209/3.1 |
| 4,515,274 | A | * | 5/1985 | Hollinger et al. | ............. 209/3.1 |
| 5,125,737 | A | * | 6/1992 | Rodriguez et al. | ............ 356/39 |
| 5,483,469 | A | * | 1/1996 | Van den Engh et al. | ...... 702/21 |
| 6,372,506 | B1 | * | 4/2002 | Norton | ........................ 436/63 |
| 7,012,689 | B2 | * | 3/2006 | Sharpe | ........................ 356/399 |

FOREIGN PATENT DOCUMENTS

| WO | 90/13368 | | 11/1990 |
| WO | 96/12173 | | 4/1996 |
| WO | WO96/12173 | * | 4/1996 |
| WO | 01/02836 | | 1/2001 |

* cited by examiner

*Primary Examiner*—Roy M Punnoose
(74) *Attorney, Agent, or Firm*—Cooley Godward Kronish, LLP (57) ABSTRACT A flow cytometer capable of forming a drop containing two or more particles comprising: (a) means (38) for moving particles in a liquid flow stream (35); (b) detector or analyser means (46A, 46B) adapted to detect or analyse particles in the flow stream; (c) waste route (39) disposed down stream from the detector or analyser means for receiving waste liquid; (d) collection route (41) disposed downstream from the detector or analyser means for receiving collection liquid containing desired particles; (e) drop forming means for dispensing a drop containing two or more particles from the collection route; and (f) controlling means (42) for directing the liquid stream to the waste route or to the collection route.

29 Claims, 3 Drawing Sheets

CYTOMETER

CROSS REFERENCE TO RELATED APPLICATIONS

This application is a National Stage Application of PCT/AU02/01454 filed Oct. 25, 2002, which claims priority to Australian Patent Application No. PR 8465, filed on Oct. 26, 2001, incorporated by reference herein in its entirety.

TECHNICAL FIELD

The present invention relates to modified cytometers, and in particular to cytometers that allow drops of liquid to be formed and collected which contain a predetermined number of particles.

BACKGROUND

Flow cytometry is used to quantitatively measure physical or chemical characteristics of particles in liquid samples as they are presented into a focused light beam. Typically, this is achieved by focusing the light beam, generated by a Mercury-Vapour lamp or a laser, onto a continuous stream of liquid, known as sheath liquid, which contains samples of particles that are injected into the sheath liquid as a narrow laminar stream. The sheath liquid passes through a flow cell where it is channelled into a fine stream normally between 50 and 250 μm in diameter. The light beam is either focused onto the stream whilst it is within a quartz region of the flow cell, or once the stream has left the flow cell. This is known as either "in quartz" analysis or "in air" analysis, respectively. The point where the light/laser strikes the stream is known as the interaction region.

As the particles pass through the flow cell they enter the light beam and scatter light. Collection optics direct the light scattered by the particles and the fluorescence light emitted by the particles into a number of light detectors. All of these light scatter and fluorescence measurements can be performed simultaneously on a single particle. The data for each parameter is normally sent in real time from the flow cytometer to a computer.

The flow rate of liquid through the focused beam is usually around 10 ms$^{-1}$ which allows a maximum of approximately 2,000 to 10,000 cells or particles to be analysed per second.

In addition to flow cytometry analysis described above, flow cytometry can be used to physically sort cells using information from the various detectors as discriminators. Sorting enables purification of a particular cell type from a mixture. The standard method of sorting cells by flow cytometry is known as droplet deflection sorting. It relies on the use of a piezoelectric transducer in the flow cell to create droplets of sheath liquid. An alternating electrical current is passed across the transducer causing the flow cell to vibrate up and down at the same frequency as the current. The vibration of the flow cell causes undulations to form in the sheath liquid once it has left the flow cell. Further downstream from the flow cell the undulations in the stream of sheath liquid become more and more defined until the stream breaks up into droplets. The last undulation in the stream before the stream breaks up into droplets is known as the last attached droplet.

If a particle is to be collected, then an electric charge is placed on the sheath liquid at the exact time the particle is in the last attached droplet. The charge occurs for the duration of one vibration of the piezoelectric crystal in the transducer. This results in a single droplet, containing the one particle to be sorted, being charged. Further downstream from the flow cell the stream of droplets passes between two plates, one positively and one negatively charged. As the charged droplet passes between the plates it is diverted from the main stream of droplets enabling it to be collected. This sorting process can be performed at a rate of several thousands times per second using a modern cytometer.

Flow cytometers that use droplet deflection sorting, however, are sophisticated instruments that require at least daily alignment by a highly skilled operator. Setting up the sorting is also difficult and requires a number of calibrations including calculation of the length of time that it takes a particle to travel from the interaction region to the last attached droplet. This length of time is known as the droplet delay. Once the sorting has been set up it has to be monitored closely to ensure that the droplet delay does not change.

A limitation of droplet deflection sorting is that it is not able to create droplets that contain more than one particle. A further problem with droplet deflection sorting is that it can create aerosols and is therefore not suitable for the analysis of biologically hazardous samples. The difficulties with the use of droplet delay sorting have restricted the use of the technology to specialised research laboratories.

An alternative form of flow cytometry sorting is described in U.S. Pat. No. 5,030,002 "Method and apparatus for sorting particles with a moving capture tube" (incorporated herein by reference). This sorting process uses a capture tube that is mechanically moved in and out of the sample stream to capture a particle. The cytometer is formed from a housing having an upper portion and a lower portion, which is shaped to form a nozzle. The lower portion of the housing is coupled to a container containing a sample liquid to be analysed. In use, the sample liquid is pumped into the housing via a tube using a pump. In addition, the housing is connected to a source of sheathing liquid, which is pumped into the housing along a tube using a pump. The upper part of the housing is connected via a tube to a waste container for catching waste sheathing liquid. The upper part of the housing is adapted to accept a capture tube. The capture tube is movable between first and second positions using an actuator, such as a solenoid or the like. The capture tube is coupled via a silicon hose to a container that collects the produced sample in a stream of liquid. In order to be able to analyse the sampled liquid, the cytometer includes a detection system formed generally from a radiation source such as a laser and one or more detectors. The detection system is adapted to detect properties of particles flowing through an interaction region. In use, the system operates to analyse individual particles contained within the sample liquid. This is achieved by having the sample liquid pumped up the tube into the housing. Simultaneously, sheathing liquid is pumped to the housing via the tube. The sheathing liquid is pumped into the housing under pressure so as to generate a focused stream of liquid surrounding the sampling liquid. As the sheathing liquid and the sampling liquid are forced through the nozzle, this causes the sampling liquid to form a thin stream containing a laminar stream of individual particles from the sample. As the sample particles pass through the interaction region, the detection system operates to analyse one or more properties of each cell or particle. A signal is then transferred via a control system to the actuator control the position of the capture tube. In use, when the capture tube is in a first position, particles contained in the laminar stream are directed through the capture tube to a collection container. When the capture tube is in a second position, the laminar stream containing particles are directed into the waste container. Accordingly, this allows the system to sort particles by detecting certain properties of the particles and then directing the particles either into a collection container or into the waste container.

In many cases, however, it is desirable to able to produce predetermined quantities and in particular predetermined concentration particles in a sample and this generally not possible with this arrangement. In particular, even when the actuator is placed in the second position, sheathing liquid will still be transmitted through the capture tube and the hose into the collection container. Accordingly, it is very difficult to direct a predetermined number of particles into the collection container and maintain a desired concentration of particles.

For example, this sorting process is utilised by the Becton Dickinson FACScalibur™ flow cytometer. This flow cytometer is simple to operate and requires no calibration or complex set-up procedure to be performed prior to sorting particles. It is simply a case of switching on the instrument, analysing a sample and sorting the particles of interest into a relatively large collection volume.

The FACScalibur™ flow cytometer has a length of silicon tubing (sort line) connected to the capture tube at the top of the flow cell. Particles sorted by the capture tube travel down this sort line into the desired type of collection vessel. As described above, there is a constant stream of sheath liquid travelling through the sort line that carries the sorted particles into the collection vessel. This constant stream of sheath liquid has to be collected along with the sorted particles resulting in the sorted particles being contained in a large volume of liquid (typically 1 to 50 ml, depending on the time of the collection process). The particles therefore have to be concentrated to much smaller volumes before they can be analysed or visualised with a microscope.

Furthermore, there are a number of applications of flow cytometry cell sorting that require sorted particles to be in a small volume of liquid. For example, the preparation of quality control samples of particles that contain an exact number of particles in a small volume of liquid. In this case, whilst a predetermined number of particles can be directed into the sort line, the particles will tend to travel along the line at different speeds because flow within the line is not laminar. The flow is slower close the wall of the line due to friction between the water molecules and the line wall. As a result, the particles become dispersed throughout the sheathing liquid and it is therefore not possible to control the concentration of the particles received at the container.

U.S. Pat. No. 5,030,002 also describes the use of a filter connected to the sort line to capture and concentrate the sorted particles. However, even using these techniques, the number of particles contained in a sample volume cannot be suitably controlled.

Accordingly, the FACScalibur™ flow cytometer cannot be used to produce droplets that contain exact numbers of particles. This is because the silicon sort line must be connected to the flow cell to carry the sorted particles away from the flow cell to a position where they can be collected. When sorted particles travel through the tubing they spread out and will no longer be in a single drop.

A flow cytometer that utilises droplet deflection sorting can be used to produce droplets that contain single particles. However, the droplet size that is produced by a cytometer that uses droplet deflection is typically limited to less than 400 µm in diameter, which can have significant disadvantages in many applications. For example, the preparation of freeze dried droplets that contain exact numbers of particles for quality control applications requires a freeze dried droplet that is large enough to be easily manipulated and visible to the human eye. Droplets from a droplet deflection cytometer are not large enough for this application. Furthermore, it is not possible to produce droplets with a droplet deflection cytometer that contain more than one particle.

Furthermore, droplet deflection sorting is less suitable as a production process than a flow cytometer that uses a catcher tube to sort particles because of the difficulties with calibrating and setting up the droplet deflection flow cytometer. In particular, a flow cytometer that utilises droplet deflection sorting requires a highly skilled operator and needs continuous monitoring during the sorting process.

The present inventors have developed modifications to a cytometer that enable defined numbers of particles in various small volumes of liquid to be formed and collected.

SUMMARY OF INVENTION

In a first aspect, the present invention provides a flow cytometer capable of forming a drop containing two or more particles comprising:

(a) means for moving particles in a liquid flow stream from a liquid source;
(b) detector or analyser means adapted to detect or analyse particles in the flow stream;
(c) waste route disposed downstream from the detector or analyser means for receiving waste liquid;
(d) collection route disposed downstream from the detector or analyser means for receiving collection liquid containing desired particles;
(e) drop forming means for dispensing a drop containing two or more particles from the collection route; and
(f) controlling means for directing the liquid stream to the waste route or to the collection route.

Preferably, the means for moving particles in a liquid flow stream is a pump.

Preferably, the detector or analyser means comprises:

(i) means for providing a beam of light to illuminate particles in the liquid flow stream;

(ii) means for detecting light with respect to each moving particle and for associating the detected light with one or more characteristics of each particle and to generate a signal responsive to the particle characteristic(s); and (iii) means for receiving the signal.

Preferably, the waste route comprises a waste tube directed to a waste collection site.

In one preferred form, the collection route comprises a capture tube having a defined volume.

In another preferred embodiment, the collection route comprises a capture tube having a defined volume and a collection tube having a defined volume passing from the collection tube.

Preferably, the drop forming means is a droplet nozzle having a defined exit aperture capable of dispensing a drop of defined volume containing two or more particles. The droplet nozzle may be positioned substantially at one end of the capture tube downstream from the detector or analyser. Alternatively, the droplet nozzle may be positioned substantially at one end of the collection tube downstream from the capture tube.

In one embodiment, the cytometer further comprises a secondary sample source capable adding liquid to or at the drop forming means. Preferably, the secondary sample source is added to the drop forming means by a suitable pump means. The secondary sample means allows for the addition of other liquids or materials to the collection liquid at or prior to the drop being formed. There are situations where materials other than those passing through the flow stream are required to be added to the particles. The secondary sample source allows the addition of material that may not be able to be passed through the cytometer. Examples include viscous liquids such as serum, coloured particulate or labile materials that may adversely affect the normal function of the cytometer. A mixer may be included within the drop forming nozzle to assist in mixing the two different liquids.

The cytometer may further comprise a droplet capture means capable of removing drops formed by the droplet nozzle. In one preferred from, the droplet capture means is a vacuum pump positioned adjacent to the droplet nozzle.

In a second aspect, the present invention provides a flow cytometer capable of forming a drop containing two or more particles comprising:

(a) a liquid source for generating a liquid stream containing particles;
(b) a detection system for detecting one or more properties of a particle contained within the liquid stream;
(c) a capture tube adapted to collect a predetermined number of particles and direct the particles to an output in a predetermined volume of liquid, the capture tube having an input for selectively receiving particles from the liquid stream, the capture tube being movable between:
  (i) a first position in which the particles contained in the liquid stream are received at the input and directed to the output, and
  (ii) a second position in which the particles are not received at the input;
(d) a control system for controlling the position of the capture tube in accordance with signals received from the detection system to thereby cause the predetermined number of particles to be collected;
(e) drop forming means for dispensing a drop containing two or more particles from the collection route; and
(f) a selector for selecting drops of liquid presented at the output in accordance with signals received from the detection system.

The cytometer preferably includes a sensor for sensing the output of each drop from the output, the selector being further adapted to selectively collect drops in accordance with signals received from the sensor.

In one preferred form, the cytometer includes, or is adapted to cooperate with, a processing system coupled to the detection system, the control system, the sensor and the selector, the processing system being adapted to:

(i) monitor for the output of a drop of liquid from the capture tube output using the sensor;
(ii) cause the control system to move the capture tube to the first position to thereby direct a particle having selected properties into the capture tube;
(iii) repeat (ii) until a predetermined number of particles have been directed into the capture tube;
(iv) control the timing of (ii) and (iii) to thereby ensure that the predetermined number of particles are contained within a single drop of liquid;
(v) monitor for the output of the drop of liquid from the capture tube output using the sensor; and
(vi) cause the selector to select the drop of liquid.

The selector usually includes:
a catching arm;
a controller for controlling the position of the catching arm, the catching arm being adapted to move between:
(i) a first position in which the drops of liquid are collected by the catching arm; and
(ii) a second position in which the drops of liquid are not collected by the collector.

The output is typically positioned below the input to allow the drops of the liquid to fall from the output under the action of gravity. The first position the collector arm is preferably positioned directly below the capture tube output, the second position being laterally spaced from the first position.

Preferably, the drop forming means is a droplet nozzle having a defined exit aperture capable of dispensing a drop of defined volume containing two or more particles. The droplet nozzle may be positioned substantially at one end of the capture tube downstream from the detector or analyser.

The drops of liquid are preferably selected when the catching arm is in the second position.

Preferably, the selected drops of liquid are processed to generate a sample. In this case, the processing typically includes immersing the drops of liquid in liquid nitrogen to form frozen sample drops. However, other forms of processing may also be used, such as placing the drops in a sample container so as to create a sample containing a predetermined number of particles.

The capture tube includes a flow path from the input to the output, the flow path typically having a defined length. Typically, a defined length of less than about 70 mm (giving a volume of about 228 µl), preferably less than about 50 mm in length (giving a volume of about 90 µl). A more preferred length being about 32 mm (giving a volume of about 170 µl). It will be appreciated that the exact length of the catcher tube flow path may vary depending on other factors, such as the diameter of the flow path.

In another preferred form, the flow cytometer does not include monitoring for drops formed. In this form, the timing of drop formation is controlled by moving the selector in the form of a vacuum line that carries liquid to waste.

The cytometers according to the present invention are suitable for forming drops of about 1 µl to 500 µl. Usually, the drops contain about 20 µl to 100 µl, more preferably the drops are about 30 µl.

The modified cytometers according to the present invention are suitable for collecting defined numbers of microorganisms such as bacteria, yeast, fungi, viruses, plant and animal cells. The cytometers are also suitable for collecting defined numbers of particles such as beads, spores, oocysts and cysts. The cytometers are also suitable for collecting defined numbers of particles such as beads that are coated or contain defined amounts of proteins, sugars, drugs, chemicals or nucleic acid. Alternatively, the particles may be granular forms of compounds such as proteins, sugars, drugs, chemicals or nucleic acid In a third aspect, the present invention provides a method for obtaining a drop of liquid having two or more particles of a desired type, the method comprising:

(a) providing a flow cytometer according to the first aspect of the present invention;
(b) providing a sample containing particles to the liquid stream;
(c) detecting or analysing the particles in the liquid stream;
(d) directing a desired type of particle to the collection route in a collection liquid;
(e) passing the collection liquid containing the desired type of particles through the drop forming means; and
(f) collecting two or more particles of a desired type in a drop.

In a fourth aspect, the present invention provides a method for obtaining a drop of liquid having two or more particles of a desired type, the method comprising:

(a) providing a cytometer according to the second aspect of the present invention;

(b) providing a sample containing particles to the liquid stream;

(c) detecting or analysing the particles in the liquid stream;

(d) directing a desired type of particle to the capture in a collection liquid;

(e) passing the collection liquid containing the desired type of particles through the drop forming means; and (f) collecting two or more particles of a desired type in a drop.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred forms will be described with reference to the following drawings and examples.

MODE(S) FOR CARRYING OUT THE INVENTION

An example of the present invention will now be described with reference to FIG. 1. As shown, one example of a flow cytometer of the present invention utilises a similar design to a cytometer known to the art. However, in contrast to prior art cytometers, the housing and its associated components are inverted so that the capture tube is located at the bottom of the apparatus. The capture tube has a droplet nozzle positioned at the distal end of the capture tube allowing the collected liquid to drip or be dispensed away from the apparatus in a drop.

Accordingly, in this example the cytometer includes a housing 31 having a lower portion. 31A and an upper portion 31B. In use, the upper portion of housing 31B is coupled to a container 33 containing a sample liquid 34 having one or more particle types, via a hose 35. This allows sample liquid 34 to be pumped into the housing 31B using a pump 36. The housing 31B is also coupled via a hose 37 to a pump 38 that is used to provide a source of sheathing liquid.

The lower portion of the housing 31A is coupled via a hose 39 to a waste container 40 for catching waste sheathing liquid. The housing 31A is also adapted to receive a capture tube 41 having an input 41A and an output 41B. The capture tube 41 is moveable between first and second positions using an actuator 42.

In order to be able to detect properties of particles contained in the sample liquid 34, the cytometer is provided with a detection system shown generally at 46. The detection system 46 includes a radiation source 46A and one or more detectors 46B. The detection system 46 operates to detect particles as they are transmitted through an interaction region shown generally at 47.

The flow cytometer may be used to analyse particles based on one or more preselected physical characteristics such as, for example, absorption at a particular wavelength, density, magnetism, specific gravity, impedance, ability to scatter light, luminescence, or fluorescence. In addition to this, the cytometer can be implemented in conjunction with Coulter sensing and Raman microscopy to analyse and sort particles.

A photodetector 46 is positioned to receive light scattered forwardly by each particle. Fluorescence, if emitted by particles energized by the illumination from the light source 46A, may also be detected. Similarly, light scattered in different directions, besides the forward direction, may be detected. In laser excited flow cytometry, both fluorescence and wide angle light scatter are typically collected at an angle whose viewing axis is 90° relative to the excitation axis of light beam. An axis of 90° viewing access for the collection of fluorescence and wide angle scatter. Thus, light travelling along the axis includes both light scatter and fluorescence as its components.

In order to collect fluorescence and light scatter at the 90° angle from the incident laser beam the light scatter and fluorescence should be separated or split. To accomplish such splitting, dichroic filters or a beam splitter is used to receive both scattered light and fluorescence at the 90° angle and to re-direct each such component in different directions. Such redirection of light scatter and fluorescence then permits the light scatter and fluorescence to be collected separately, even though both originate at the 90° angle.

For example, the reflected light scatter may be detected by a photomultiplier tube. If the fluorescence includes a number of different color regions, a dichroic mirror may be used to separate the different color wavelengths. Thus, for example, fluorescence in the green color region may be transmitted by a dichroic mirror along axis and collected in an appropriate photodetector. Additional dichroic mirrors may be included as in U.S. Pat. No. 4,662,742 for associating the fluorescence colors with additional characteristics of cells or particles analyzed. Those skilled in the art will appreciate that various lenses, filters, barriers or the like may be employed in conjunction with each additional photodetector to obtain as pure a signal as possible. Obtaining such optically clean signals is most desirable particularly when fluorescence and light scatter channels are used.

The electrical signals from photodetectors are typically fed as discrete pulses to the electronics of the apparatus for purposes of display, storage or further processing so that one or more characteristics of the particles under analysis can be determined or sorted. Electronics may be included in an analysis console, if desired.

While a single specific preselected characteristic of a given particle may be used for analysis in this type of configuration, it is also possible to use multi-parameter flow cytometry. "Multi-parameter flow cytometry" is used herein to mean the measurement of several characteristics of a particular particle to differentiate it from another.

The techniques available to analyse particles using flow cytometry are well documented in the art. However, by way of exemplification, where one wishes to rely on optical analysis, a sample containing particles may be mixed with one or more dyes, fluorescent or luminescent agents, or antibodies conjugated to such agents, for example, prior to analysis via flow cytometry so that specific particles are stained or tagged. An example of such a process involves the use of the dye fluorescein diacitate which specifically stains viable cells. Following staining with fluorescein diacitate, the sample may be analysed and single viable particles that are at a specific stage of their life cycle identified.

In any event, in use, sample liquid 34 containing one or more particle types is pumped along tube 35 into the housing 31B. At this point, sheathing liquid is added to provide a focused stream that surrounds the sample liquid. The stream is forced through the aperture 32 of the housing 31B to create a fine stream of between 50 and 250 micrometers in diameter including a laminar stream of individual particles from the sample 34.

The liquid passes through the interaction region 47 allowing the properties of individual particles to be measured using detection system 46. The detection system 46 is then used to operate the actuator 42 allowing the capture tube 41 to be moved between first and second positions. When the capture tube 41 is in a first position, the particles are collected at the capture tube input 41A and directed through the capture tube 41. In contrast, when the capture tube is in a second position, the particles are directed via the tube 39 into the waste container 40. It will be appreciated that in either catching position, sheath liquid will additionally be directed along the capture tube.

A drop forming means in the form of a droplet nozzle 70 is disposed at the distal end 41B of the capture tube 41. The droplet nozzle is adapted to form a drop of a defined volume.

Accordingly, in use, the cytometer can be used to create samples containing only particles with certain properties in a manner similar to prior art cytometers. However, in addition, the flow path between the input 41A and the output 41B of the capture tube 41 is typically limited to a defined short length to define a small volume. Typically the defined short length of less than 70 mm (giving a volume of about 228 µl), and is preferably less than 50 mm in length (giving a volume of about 90 µl), with the more preferred length being about 32 mm (giving a volume of about 170 µl). As a result, any particles caught by the capture tube do not become distributed within the sheath liquid contained in the capture tube flow path. Instead, the particles tend to emerge within the same small volume of sheath liquid in which they were captured.

Accordingly, this makes it possible to capture individual drops containing a predetermined number of particles. In order assist in this function, the cytometer can be additionally or optionally provided with a drop detector 50, a sample container 51, and a catcher 52, which is coupled to an actuator 53.

The drop detector is typically an optical detection system that is capable of detecting drops of liquid created at the output 41B. The drop detector is adapted to cooperate with the catcher 52, which can be selectively moved between a first position (shown in normal lines) and a second position (shown in dotted lines), so as to selectively catch the drops.

Accordingly, when it is desired to collect a sample containing a predetermined number of particles, the cytometer is configured to operate to generate drops of liquid which are then selectively caught by the catcher 52. In order to achieve this, the cytometer is initially activated with the capture tube 41 in a second position so that no particles, even particles containing the desired properties are collected. When the drop detector 50 detects that a drop has just been output from the output 41B, the capture tube 41 is activated to capture a particle that has the desired properties. This process is repeated until the predetermined number of particles have been captured. Thus, in general a single movement of the capture tube will only catch one particle, with the movement being repeated rapidly (up to 300 per second) to catch multiple particles in a single drop of sheath liquid. These particles are caught in the capture tube 41 and directed along the flow path to the drop forming means 70 at the output 41B. The particles and the surrounding sheath liquid then form a new drop at the drop forming means 70 at the output 41B of the capture tube 41. This procedure is continued until the predetermined number of particles captured by the capture tube 41. The drop will then continue to fill with sheathing liquid until finally the drop has sufficient volume and falls from the capture tube at means 41B. As the flow path length of the capture tube is only small, there is insufficient travel length for the particles to become spread out and distributed through a number of different drops. Accordingly, the created drop contains the required number of particles. Thus, the capture is adapted to ensure that a predetermined number of particles may be captured within a predetermined volume of sheathing liquid.

The catcher 52 can be used to allow the collection of the created drops. This can be achieved for example by activating the actuator 53 to cause the catcher 52 to move into the second position, as the drop falls, thereby causing the catcher to catch the drop. One problem with this technique, however, is that it is very difficult to handle individual drops of liquid. In particular, when the catcher 52 catches the drops of liquid, it is difficult to extract the liquid drop from the catcher. This can be aided by having the catcher provided with a low friction surface to aid in drop delivery. Even in this modification, it is possible for a fragment of the drop to become left behind on the catcher when the drop is subsequently extracted. This could effect the number of particles contained in the drop, thereby making the sample unusable.

In order to avoid this problem, the sample container 51 can be filled with a cryogenic liquid, such as liquid nitrogen or the like. In this case, the unwanted drops are collected by the catcher and removed. The drops containing the desired particles are allowed to fall into the sample container 51. The liquid nitrogen will cause the liquid drop to freeze instantly thereby producing a frozen droplet containing a predetermined number of particles.

The frozen particles can then be removed from the liquid nitrogen and dried in accordance with a drying technique known in the art. Accordingly, this allows frozen drops containing a desired number of particles to be collected.

In general, the temperature of the cryogen should be selected such that the particles being collected are not damaged. Accordingly, the temperature of the cryogen will typically be selected depending on the type of particle being collected (ie. cells, enzymes, proteins, or the like), as well as on the specific variety (ie. the particular cell being collected).

An example of the freeze drying process is described in more detail in PCT/AU02/01216 entitled "Products Comprising Quantum of Bioparticles and Method For Production Thereof". The system was tested by using a FACScalibur™ flow cytometer that had been inverted.

Figure 1:
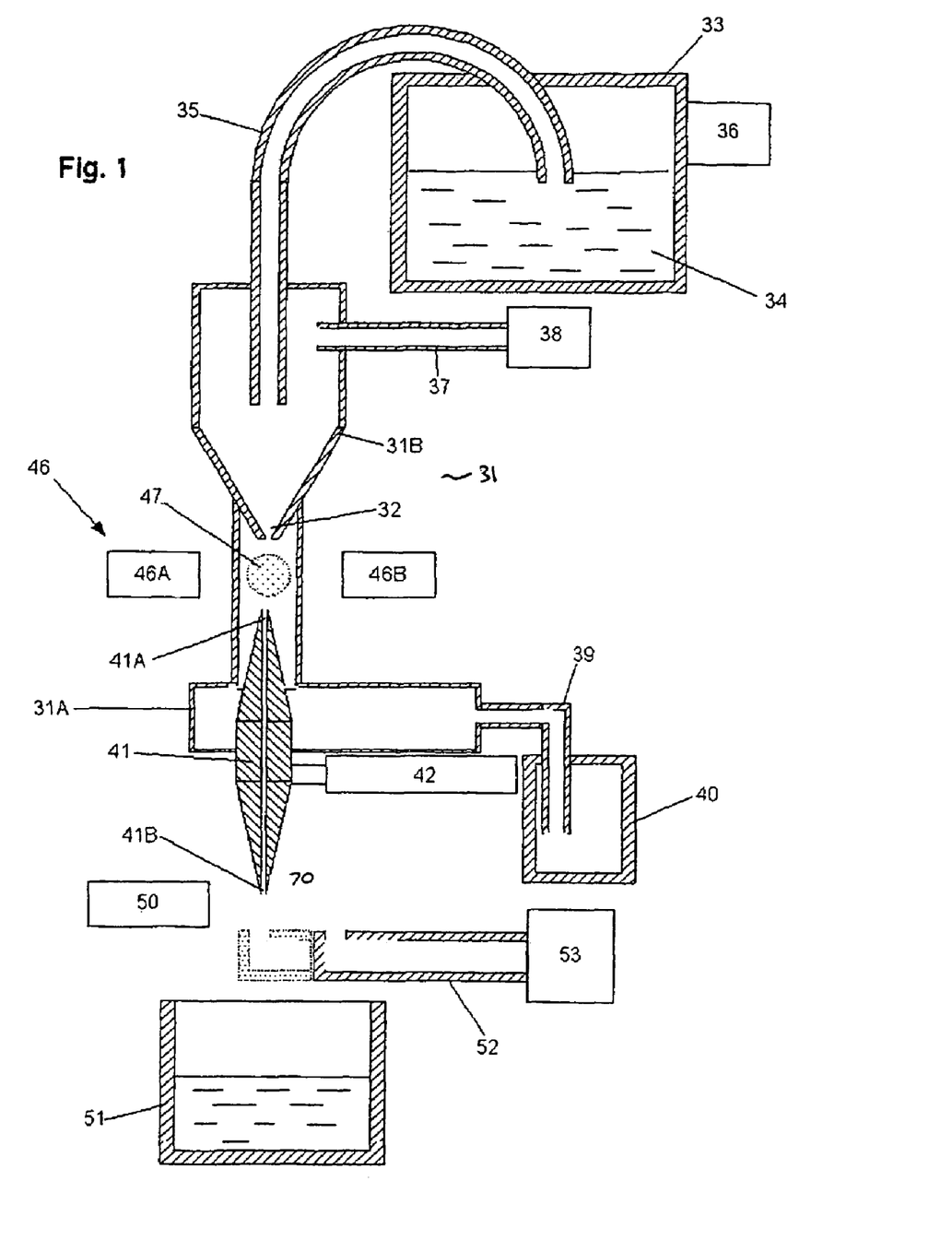
FIG. 1 is a schematic diagram of one cytometer according to the present invention having a drop forming means positioned at one end of a capture tube.
Figure 2:
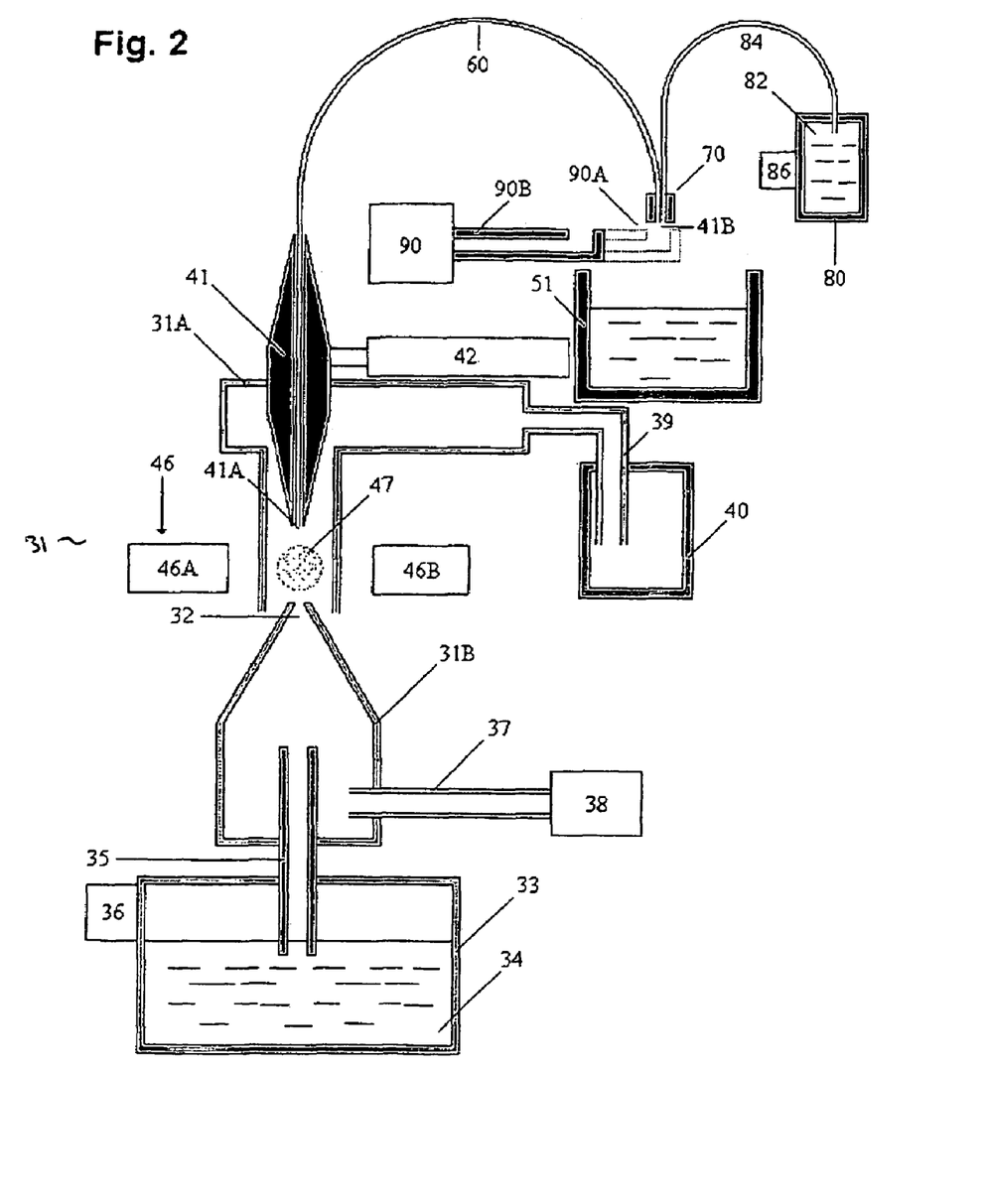
FIG. 2 is a schematic diagram of a further cytometer according to the present invention having a drop forming means positioned at one end of a collection tube connected to a capture tube. The cytometer also includes means for adding additional liquid to the drop forming means.

FIG. 2 shows an arrangement of a second preferred embodiment of a flow cytometer according to the present invention having a collection tube attached to a capture tube. This arrangement differs from the example described above in that it is not an inverted instrument. The numbering used is similar to the numbering of FIG. 1 for the same functioning components.

Accordingly, in this example the cytometer includes a housing 31 having a first portion 31A and a second portion 31B. In use, the first portion of housing 31B is coupled to a container 33 containing a sample liquid 34 having one or more particle types, via a hose 35. This allows sample liquid 34 to be pumped into the housing 31B using a pump 36. The housing 31B is also coupled via a hose 37 to a pump 38 that is used to provide a source of sheathing liquid.

The second portion of the housing 31A is coupled via a hose 39 to a waste container 40 for catching waste sheathing liquid. The housing 31A is also adapted to receive a capture tube 41 having an input 41A The capture tube 41 is moveable between first and second positions using an actuator 42.

A stainless steel tube 60 is inserted into the capture tube 41 forming a collection route. The stainless steel tube 60 begins at the capture tube input 41A and ends at a droplet nozzle 70. This increases the length of the collection route and decreases the internal diameter of the capture tube 41. The output of the capture tube 41B is extended to the droplet nozzle 70. The droplet nozzle 70 forms drops containing the desired number of particles in a defined volume.

In order to be able to detect properties of particles contained in the sample liquid 34, the cytometer is provided with a detection system shown generally at 46. The detection system includes a radiation source 46A and one or more detectors 46B. The detection system 46 operates to detect particles as they are transmitted through an interaction region shown generally at 47.

The flow cytometer may be used to analyse particles based on a number of preselected physical characteristics such as, for example, absorption at a particular wavelength, density, magnetism, specific gravity, impedance, ability to scatter light, luminescence, or fluorescence. In addition to this, the present invention can be implemented in conjunction with Coulter sensing and Raman microscopy to analyse and sort particles.

While a single specific preselected characteristic of a given particle may be used for analysis in this type of configuration, it is also possible to use multi-parameter flow cytometry. "Multi-parameter flow cytometry" is used herein to mean the measurement of several characteristics of a particular particle to differentiate it from another.

In any event, in use, sample liquid is pumped along tube 35 into the housing 31B. At this point, sheathing liquid provides a focused stream that surrounds the sample liquid. The stream is forced through the aperture 32 to create a fine stream of between 50 μm and 250 μm in diameter including a laminar stream of individual particles from the sample.

The liquid passes through the interaction region 47 allowing the properties of individual particles to be measured using detection system 46. The detection system 46 is then used to operate the actuator 42 allowing the capture tube 41 to be moved between first and second positions. When the capture tube 41 is in a first position, the particles are collected at the capture tube input 41A and directed through the capture tube 41. In contrast, when the capture tube is in a second position, the particles are directed via the tube 39 into the waste container 40. It will be appreciated that in either catching position, sheath liquid will additionally be directed along the capture tube.

In order to allow the addition of further liquid to the drop, a secondary sample source 80 containing secondary sample liquid 82 connected to the droplet nozzle 70 via a secondary sample tube 84. Secondary sample pump 86 allows the addition of defined amount of a secondary sample liquid 82 to the drop.

In order to control the number drops formed and collected, the cytometer further includes capture means 90 in the form of a vacuum pump positioned close to the droplet nozzle 70 in position 90A or can be activated to position it away from the droplet nozzle 70 in position 90B. The capture means 90 is activated when drops being formed are not needed to be collected. When a drop has the required number or type of particle, the capture means 90 is inactivated and drops form and drop into the required vessel 51.

Figure 3:
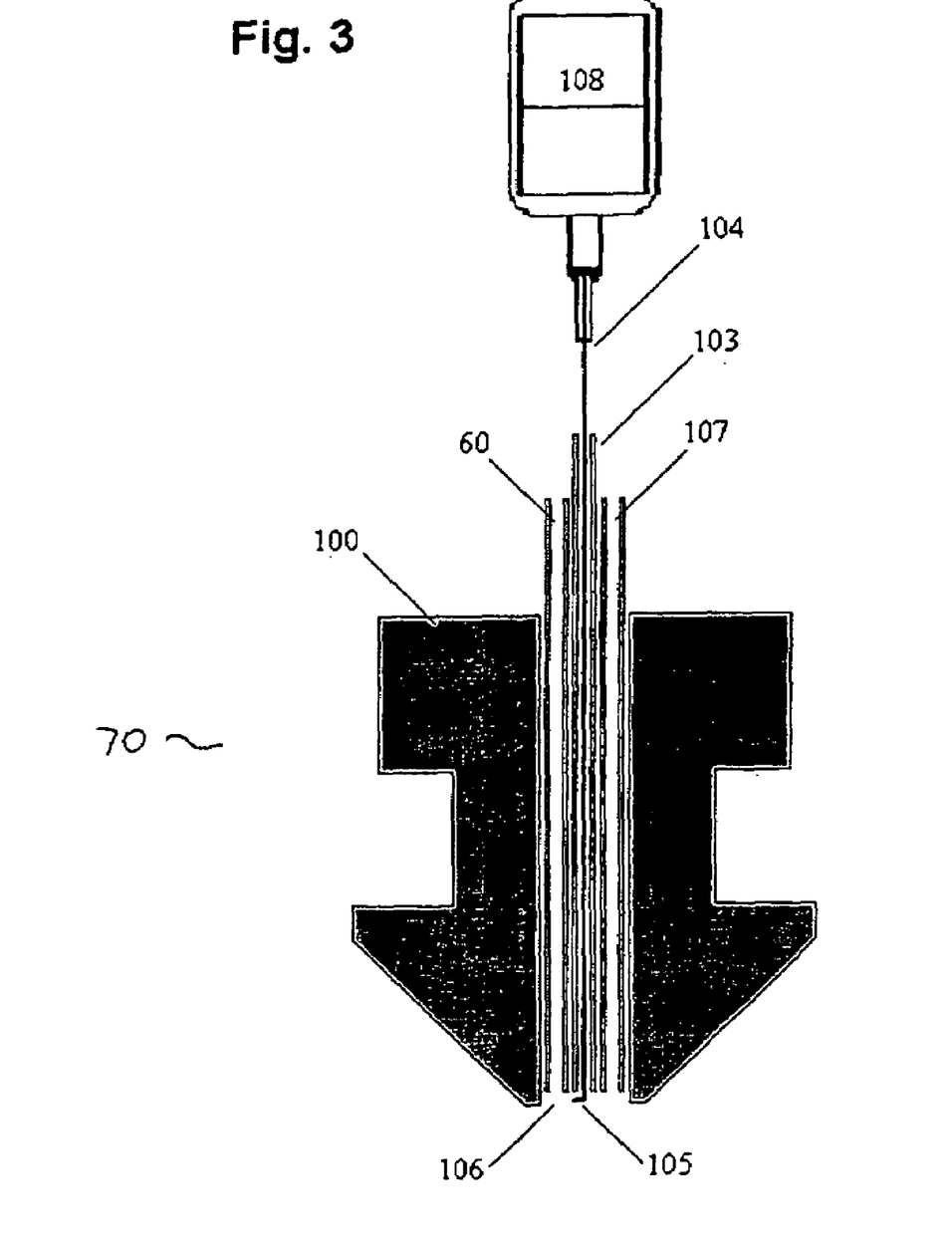
FIG. 3 is a schematic diagram of droplet nozzle having a secondary sample source capable adding liquid to or at the drop forming means together with a mixer to assist in mixing the two different liquids.

The droplet nozzle 70 is described in further detail in relation to FIG. 3. A nozzle housing 100 is in the form of a plastic nipple into which three hypodermics are fitted. One of the hypodermics is the capture tubing 60. A second hypodermic 107 is connected to a secondary sample source 80 containing secondary sample liquid 82 connected to the dropper nozzle 70 via a secondary sample tube 84. Secondary sample pump 86 allows the addition of defined amount of a secondary sample liquid 82 to the drop.

A center hypodermic 103 acts as a housing for a wire 104 that is used to mix the droplet. At the lower end, the wire is bent at right angles 105 as it exists the centre hypodermic 104. The wire 104 is connected to an electric motor 108 that spins the wire at a rate of approximately 900 rpm.

Accordingly, in use, the cytometer can be used to create samples containing only particles with certain properties. However, in addition, the flow path between the input 41A and the output 41B of the collection tube 60 is typically limited to a defined length and a defined internal diameter. The length and internal diameter of the capture tube 41 are controlled by inserting tubing 60 into the capture tube 41. The length and the internal diameter of the tubing 60 are important for producing drops that contain defined numbers of particles. The selection of the correct length and internal diameter of the tubing 60 enables the following three functions:

I. the flow rate through the capture tube 41 should not be restricted to such an extent that liquid is diverted to the waste tank 51 instead of into the capture tube 41;
II. the length of the tubing should be sufficient to clear the flow cytometer;
III. the internal diameter should not be too large so that particles become diluted into a volume of liquid that is too large to form a suitable drop.

The preferred length of the tubing 60 is 170 mm with an internal diameter of about 241 μm. This length is sufficient to clear the cytometer by carefully bending the tubing into a U shape. The cytometer can therefore be operated in its normal orientation. The tubing should not be kinked or bent into sharp angles, as this can introduce turbulence into the liquid stream within the tubing and result in sorted particles spreading out as they travel through the tubing. This tubing enables sorted particles to be formed into a droplet at the droplet forming nozzle 70.

A shorter length of tubing will function correctly but it may be difficult to clear the cytometer without introducing kinks into the tubing.

If the internal diameter of the tubing is less than about 112 µm, the capture tube may not capture the desired particles. A very small diameter of the tubing can restrict the flow of liquid into the capture tube to such an extent that liquid is diverted to the waste container. This results in the desired particles entering the waste container and being lost.

If the internal diameter of the tubing is greater than about 350 µm, then the sorted particles can become spread through a volume of liquid that is too large to form into a single droplet.

The precise control of timing the sorting and of forming the drop is important to ensure that the drop contains the defined number of particles. A signal is sent to the cytometer to begin sorting the defined number of particles. There is a delay of approximately 50 ms during which the cytometer prepares to start sorting. The cytometer then starts sorting particles at a rate of approximately 250 per second. The sorted particles travel down the capture tubing to the drop forming nozzle. It is important that the catcher means moves out from the nozzle and allows the drop to start forming immediately before the sorted particles reach the drop forming nozzle. If the catcher means moves too late, then sorted particles will go to waste and will not be in the droplet. If the catcher means moves too early and the drop starts forming before the sorted particles have almost reached the nozzle, then the formation of the drop may be completed before all sorted particles have reached the nozzle. This would result in the drop breaking off before all sorted particles were within the drop. It takes approximately 0.66 s for the drop to form and break off.

The sorting process involves a delay of approximately 50 ms and then a sorting period of approximately 4 ms per particle. Therefore, the length of time required to sort 30 particles is approximately 170 ms. As the sorted particles travel down the capture tubing forming the collection route to the drop forming nozzle the particles tend to become spread out by turbulence in the tubing. The amount of spreading varies depending on the internal diameter of the capture tubing and the length of the capture tubing. The length of time that it takes particles to reach the drop forming nozzle also depends on the internal diameter of the capture tubing and the length of the capture tubing When using the preferred capture tubing of length of 170 mm with an internal diameter of 241 µm, the particles arrive at the drop forming nozzle with the first and last particle separated by approximately 250 ms. The length of time that it takes the sorted particles to travel through this capture tubing is approximately 50 ms.

To produce a drop that contains 30 sorted particles using the preferred capture tubing, the capture means must be moved away from the drop forming nozzle no later than 100 ms. Typically a delay of 50 ms is used.

An alternative embodiment of this invention utilises an electrostatic sorter to form drops that contain more than one particle. Electrostatic sorters such as a Becton Dickenson Facstarplus™, a Becton Dickenson Advantage or a Coulter Elite enable particles to be sorted in small drops of liquid. However, the production of drops that contain more than one particle is not possible. The drop forming device developed by the present inventors could be used to collect multiple drops from an electrostatic sorter and form them into a single drop.

Examples of use of two cytometers according to the present invention are described below.

EXAMPLE 1

Instrumentation

The cytometer was a modified FACScalibur™ flow cytometer as shown in FIG. 1. The instrument was inverted by using an aluminium frame that enclosed the FACScalibur™ flow cytometer. The lid of the flow cytometer was removed, and the bottom of the cytometer was bolted to the frame and the frame and cytometer were then inverted. The instrument was capable of forming drops containing two or more particles.

An optical sensor (Festo, Sydney) was positioned directly below the output of the capture tube and adjusted to enable detection of drops as they formed at the end of the capture tube. On the formation of a droplet, the optical sensor was activated sending a pulse signal via a Programmable Logic Controller (PLC) model FC-30 (Festo) to a catcher delay and enabling it and also sending a pulse signal to a modified Macintosh mouse as described in. WO 01/68902 to acquire sort data. The time that the sorted particles travelled from the inspection region of the flowcell to the exit point of the catcher was noted as the catcher delay. Once the catcher delay is timed down, the catcher arm was removed from the drop path, and a catcher arm delay is enabled. The catcher arm was designed as a vacuum waste system to exit unwanted drops. The time taken for a single droplet to pass the catcher arm was noted as the catcher arm delay. Once the catcher arm delay is timed down, the cycle is reset and the optical sensor is re-enabled.

The sample container, the container containing the sheath liquid and the waste container were inverted so that the waste tanks were upright. The optics cover and the sort line were removed. The sheath tank was filled with MilliQ water.

Analysis of *Eschericia coli*

A strain of *E. coli* (ATCC 11775) was grown by vigorously in shaking a flask of nutrient broth at 37° C. for 5 hours. The sample was diluted 1 in 1000 into filtered (0.22 µm) phosphate buffered saline (PBS). A 200 µl sample of the *E. coli* was taken up into a pipette tip that was attached to the sample insertion rod via a 4 mm length of silicon tubing. A 150 mm length of silicon tubing with an internal diameter of 10 mm was sealed at one end and then placed over the sample and the sample insertion rod. This allowed the sample to be pressurised by the cytometer.

The cytometer was used with the detectors set at the following levels of sensitivity:

| Forward scatter | E002 |
| Side scatter | 500 |

Side scatter was used as the Threshold at a value of 350.

A region was defined on a scatter plot of Side scatter verses Forward scatter that contained the *E. coli*. This region was then used to sort the *E. coli*.

Sorting the *E. coli*

The cytometer was set to sort 30. *E. Coli*/cells. The flow rate and the concentration of the *E. coli* were adjusted to ensure that the sort rate was between 150 and 200 sorts per second.

The droplet that formed immediately after the sorting was completed was collected onto nutrient agar plates, spread with a sterile plastic L-shaped rod and incubated at 37° C. overnight. Thirty *E. coli* colonies were detected on the agar plates.

EXAMPLE 2

Instrumentation

A Becton Dickinson FACScalibur™ flow cytometer was modified according to the cytometer shown in FIG. 2 and FIG. 3. The cytometer was calibrated to enable 30 *Bacillus cereus* spores to be dispensed within a single droplet. Serum was injected into the droplet whilst it was forming to enable production of droplet that freeze dries into a substantially spherical ball.

The modification involved inserting into the capture tube within the flow cell a 40 mm length of hypodermic tubing with an external diameter of 296 µm and an internal diameter of 165 µm (A-M Systems, Calsborg, USA). A 265 mm length of silicon tubing with an internal diameter of 165 µm was connected to the hypodermic needle (A-M System, Calsborg, USA). A 30 mm length of hypodermic tubing, internal diameter 165 µm was connected to other end of the silicon tubing (A-M System, Calsborg, USA). This modification allowed the capture of a drop having about 27 µl. The drop was formed in a droplet nozzle that consisted of a 5 mm polypropylene barbed fitting (Becton Dickinson, San Hose, USA) into which the hypodermic from the cytometer was inserted. When the cytometer was turned on, drops were formed at the end of the hypodermic tubing from the nozzle.

A peristaltic pump (Cole Parmer Instruments, Illinois, USA) was used to inject horse serum through a 300 mm length of hypodermic tubing (A-M System, Calsborg, USA) with internal diameter 165 µm, which was also inserted into the droplet nozzle (as depicted in FIG. 3) so that the serum can be mixed with the output of the flow cytometer to form drops. The flow rate of the pump was adjusted to match the flow rate of the liquid exiting the cytometer sort line. A mixer was incorporated into the nozzle by inserting a third hypodermic (305 µm internal diameter, Small Parts Inc.) into the nozzle and then inserting a finer hypodermic (external diameter 254 µm, Small Parts Inc.) into this hypodermic. A 1 mm length of the fine hypodermic was bent into a right angle to form a hook at the exit of the outer hypodermic. The fine hypodermic was attached to an electric motor and spun at an rpm of approximately 900.

The peristaltic pump was stand-alone unit with coarse speed dial to control the beginning of droplet formation, a 6 psi micro bore double acting pneumatic cylinder (Asco, Frenchs Forest, NSW, Australia) was used with an attached polypropylene vacuum nozzle. The vacuum nozzle attached to the end of the shaft of the cylinder was held near the droplet nozzle exit point. The vacuum nozzle ensured that all liquids received from the droplet nozzle were sent to waste before droplet formation began. On activation of the double acting cylinder, the vacuum nozzle was removed therefore allowing a droplet to immediately form directly after removal.

The pneumatic cylinder was controlled by a Programmable Logic Controller (PLC) model FC-30 (Festo). The PLC also controlled the sorting process of the cytometer via a modified Macintosh mouse as described in WO 01/68902. Normal operation of the cytometer sorting process was performed by clicking a mouse. Basically, the mouse was modified to accept a 0.1 s long 24V pulse signal from the PLC which mimics a mouse click and begins the cytometer sorting process.

A push button switch was connected to the PLC. A program was written for the PLC that waited for the button to be pushed and then begum a cycle that involved the following steps:

In order for a sort and sample to be prepared in drop form, the following steps were carried out:

I. activating the sort process through the mouse;
II. waiting a predefined delay that is sufficient for the first sorted particle to reach the droplet formation point;
III. activating the pneumatic cylinder to remove the vacuum nozzle away from the liquid flow;
IV. waiting a predefined delay that is sufficient to allow a single drop to form and break away; and
V. activating the pneumatic cylinder to move the vacuum nozzle into the liquid flow.

Sorting 30 *E. coli* into a Single Drop

Preparation of *E. coli*

A strain of *E. coli* (NCTC 9001) was grown at 37° C. for 24 hours in 1.6% (w/v) tryptone and 1% (w/v) yeast extract at pH 7.2. The cells were diluted 1 in 1000 in filtered (0.22 µm) PBS and analysed immediately.

Analysis of *E. coli*

A region was defined on a scatter plot of Side scatter verses Forward scatter that contained the *E. coli*. This region was then used to sort the *E. coli*.

Selection of Desired *E. coli*

The cytometer was set according to the manufacturer's instructions to sort samples of 30 *E. coli* cells. The flow rate and the concentration of the *E. coli* were adjusted to ensure that the sort rate was between 220 and 250 sorts per second. Droplets were collected onto nutrient agar plates (Oxoid Ltd), allowed to dry at room temperature for 30 minutes and then incubated at 37° C. for 12 hours The agar plates were then examined and were observed to contain between 27 and 30 *E. coli* colonies.

Freezing and Freeze-Drying the Droplets

Droplets from the cytometer were collected into test tubes that contained liquid nitrogen. The droplets were frozen as spheres or balls. After collection of the droplets, the tubes were placed in a Dynavac FD12 freeze dryer and dried overnight at a vacuum of $2 \times 10-1$ Torr and a condenser temperature of −70° C.

The next day, the vials were capped under vacuum and removed from the freeze drier. The vials were opened and the balls individually placed onto nutrient agar plates (Oxoid, Australia), and 200 µl of sterile 0.9% saline was carefully pipetted onto each ball. The balls were allowed to rehydrate for 5 min and then spread with a sterile plastic spreader. After incubation at 37° C. for 12 hours the agar plates were examined and were observed to contain between 25 and 30 *E. coli* colonies.

EXAMPLE 3

*E. coli* were cultured, analysed and droplets produced that contained 30 *E. coli* as described in Example 2.

Freezing and Freeze-Drying the Droplets

Droplets from the cytometer were collected into test tubes that contained liquid nitrogen. After collection of the droplets, the tubes were placed in a Dynavac FD12 freeze dryer and dried overnight at a vacuum of $2 \times 10^{-1}$ Torr and a condenser temperature of −70° C. The next day, the vials were capped under vacuum and removed from the freeze drier. The vials were opened and the balls individually placed onto nutrient agar plates (Oxoid, Australia), and 200 µl of sterile 0.9% saline was carefully pipetted onto each ball. The balls were allowed to rehydrate for 5 min and then spread with a sterile plastic spreader. After incubation at 37°

C. for 12 hours the agar plates were examined and were observed to contain between 25 and 30 *E. coli* colonies.

Persons skilled in the art will appreciate that numerous variations and modifications will become apparent. All such variations and modifications which become apparent to persons skilled in the art, should be considered to fall within the spirit and scope that the invention broadly appearing before described.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A flow cytometer which forms a drop containing two or more particles of a predetermined type, or size, or volume, or shape comprising:
   (a) means for moving particles in a liquid flow stream from a liquid source;
   (b) detector or analyser means adapted to detect or analyse particles in the flow stream;
   (c) waste route disposed downstream from the detector or analyser means for receiving waste liquid;
   (d) collection route disposed downstream from the detector or analyser means for receiving collection liquid containing desired particles;
   (e) drop forming means for dispensing a drop containing two or more particles of a predetermined type, or size, or volume, or shape from the collection route; and
   (f) controlling means for directing the liquid stream to the waste route or to the collection route.

2. The cytometer according to claim 1 wherein the means for moving particles in a liquid flow stream is a pump.

3. The cytometer according to claim 1 wherein the detector or analyser means comprises:
   (i) means for providing a beam of light to illuminate particles in the liquid flow stream;
   (ii) means for detecting light with respect to each moving particle and for associating the detected light with one or more characteristics of each particle and to generate a signal responsive to the particle characteristic(s); and
   (iii) means for receiving the signal.

4. The cytometer according to claim 1 wherein the waste route comprises a waste tube directed to a waste collection site.

5. The cytometer according to claim 1 wherein the collection route comprises a capture tube having a defined volume.

6. The cytometer according to claim 1 wherein the collection route comprises a capture tube and a collection tube having a defined volume passing from the capture tube.

7. The cytometer according to claim 1 wherein the drop forming means is a droplet nozzle having a defined exit aperture capable of dispensing a drop of defined volume containing two or more particles of a predetermined type, or size, or volume, or shape.

8. The cytometer according to claim 7 wherein the droplet nozzle is positioned substantially at one end of the capture tube.

9. The cytometer according to claim 7 wherein the droplet nozzle is positioned substantially at one end of the collection tube.

10. The cytometer according to claim 9 further comprising a secondary sample source capable adding liquid to the droplet nozzle.

11. The cytometer according to claim 10 wherein the secondary sample source is added to the droplet nozzle by a pump means.

12. The cytometer according to claim 1 further comprising a droplet capture means capable of removing drops formed by the droplet nozzle.

13. The cytometer according to claim 12 wherein the droplet capture means is a vacuum pump positioned adjacent to the droplet nozzle.

14. The cytometer according to claim 1 which forms a drop having a volume of between 1 µl and 500 µl.

15. The cytometer according to claim 14 wherein the drop has a volume of between 20 µl and 100 µl.

16. The cytometer according to claim 15 wherein the drop has a volume of about 30 µl.

17. A method for obtaining a drop of liquid having two or more particles of a predetermined type, or size, or volume, or shape, the method comprising:
   (a) providing a cytometer according to claim 1;
   (b) providing a sample containing particles to the liquid stream;
   (c) detecting or analysing the particles in the liquid stream;
   (d) directing a desired type of particle to the collection route in a collection liquid;
   (e) passing the collection liquid containing the desired type of particles through the drop forming means; and
   (f) collecting two or more particles of a predetermined type, or size, or volume, or shape in a drop.

18. A flow cytometer which forms a drop containing two or more particles of a predetermined type, or size, or volume, or shape comprising:
   (a) a liquid source for generating a liquid stream containing particles;
   (b) a detection system for detecting one or more properties of a particle contained within the liquid stream;
   (c) a capture tube adapted to collect a predetermined number of particles and direct the particles to an output in a predetermined volume of liquid, the capture tube having an input for selectively receiving particles from the liquid stream, the capture tube being movable between:
      (i) a first position in which the particles contained in the liquid stream are received at the input and directed to the output, and
      (ii) a second position in which the particles are not received at the input;
   (d) a control system for controlling the position of the capture tube in accordance with signals received from the detection system to thereby cause the predetermined number of particles to be collected; and
   (e) drop forming means for dispensing a drop containing two or more particles from the collection route.

19. The cytometer according to claim 18 further including a sensor for sensing the output of each drop from the output, the cytometer being further adapted to selectively collect drops in accordance with signals received from the sensor.

20. The cytometer according to claim 19 wherein the cytometer includes:
   (a) a catching arm;
   (b) a controller for controlling the position of the catching arm, the catching arm being adapted to move between:
      (i) a first position in which the drops of liquid are collected by the catching arm; and
      (ii) a second position in which the drops of liquid are not collected by the collector.

21. The cytometer according to claim 20 wherein the droplet nozzle is positioned substantially at one end of the capture tube downstream from the detector or analyser.

22. The cytometer according to claim 18 further including or is adapted to cooperate with; a processing system coupled to the detection system, the control system and the sensor, the processing system being adapted to:
   (i) monitor for the output of a drop of liquid from the capture tube output using the sensor;
   (ii) cause the control system to move the capture tube to the first position to thereby direct a particle having selected properties into the capture tube;
   (iii) repeat (ii) until a predetermined number of particles have been directed into the capture tube;
   (iv) control the timing of (ii) and (iii) to thereby ensure that the predetermined number of particles are contained within a single drop of liquid;
   (v) monitor for the output of the drop of liquid from the capture tube output using the sensor; and
   (vi) collect the drop of liquid.

23. The cytometer according to claim 18 wherein the drop forming means is a droplet nozzle having a defined exit aperture capable of dispensing a drop of defined volume containing two or more particles.

24. The cytometer according to claim 18 further comprising a droplet capture means capable of removing drops formed by the droplet nozzle.

25. The cytometer according to claim 24 wherein the droplet capture means is a vacuum pump positioned adjacent to the droplet nozzle.

26. The cytometer according to claim 18 which forms a drop having a volume of between 1 µl and 500 µl.

27. The cytometer according to claim 26 wherein the drop has a volume of between 20 µl and 100 µl.

28. The cytometer according to claim 27 wherein the drop has a volume of about 30 µl.

29. A method for obtaining a drop of liquid having two or more particles of a predetermined type, or size, or volume, or shape of, the method comprising:
   (a) providing a cytometer according to claim 18;
   (b) providing a sample containing particles to the liquid stream;
   (c) detecting or analysing the particles in the liquid stream;
   (d) directing a desired type of particle to the collection route in a collection liquid;
   (e) passing the collection liquid containing the desired type of particles through the drop forming means; and
   (f) collecting two or more particles of a predetermined type, or size, or volume, or shape in a drop.

* * * * *